US00PP23637P2

(12) United States Plant Patent
Hofmann et al.

(10) Patent No.: US PP23,637 P2
(45) Date of Patent: May 28, 2013

(54) ***PELARGONIUM* PLANT NAMED 'KUEGRAPIDUE'**

(50) Latin Name: *Pelargonium crispum*
Varietal Denomination: Kuegrapidue

(75) Inventors: Christa Hofmann, Leipzig (DE); Klaus Olbricht, Dresden (DE); Katrin Meinl, Dresden (DE); Michael Wiedemann, Dresden (DE)

(73) Assignee: Kühne Jungpflazen GbR Clauss & Torsten Kühne, Dresden (DE)

( * ) Notice: Subject to any disclaimer, the term of this patent is extended or adjusted under 35 U.S.C. 154(b) by 0 days.

(21) Appl. No.: 13/374,293

(22) Filed: Dec. 20, 2011

(51) Int. Cl.
*A01H 5/00* (2006.01)

(52) U.S. Cl.
USPC ..... Plt./324

(58) Field of Classification Search ..... Plt./324
See application file for complete search history.

*Primary Examiner* — Annette Para
(74) *Attorney, Agent, or Firm* — C. A. Whealy

(57) ABSTRACT

A new and distinct cultivar of *Pelargonium* plant named 'Kuegrapidue', characterized by its compact and mounding plant habit; freely branching habit; pinching is not required; freely flowering habit; light purple and red purple bi-colored flowers; no requirement for cooling treatment for flower initiation and development; and good container and garden performance.

1 Drawing Sheet

Botanical designation: *Pelargonium crispum*.
Cultivar denomination: 'KUEGRAPIDUE'.

BACKGROUND OF THE INVENTION

The present invention relates to a new and distinct cultivar of *Pelargonium* plant, botanically known as *Pelargonium crispum* and hereinafter referred to by the name 'Kuegrapidue'.

The new *Pelargonium* plant is a product of a planned breeding program conducted by the Inventors in Dresden, Germany. The objective of the breeding program is to develop new *Pelargonium crispum* plants with uniform growth habit and unique flower colors.

The new *Pelargonium* plant originated from a cross-pollination made by the Inventors in Dresden, Germany in 2007 of two unnamed proprietary selections of *Pelargonium crispum*, not patented. The new *Pelargonium* plant was discovered and selected by the Inventors as a single flowering plant from within the progeny of the stated cross-pollination in a controlled greenhouse environment in Dresden, Germany in June, 2008.

Asexual reproduction of the new *Pelargonium* plant by vegetative terminal cuttings in a controlled greenhouse environment in Dresden, Germany since August, 2008, has shown that the unique features of this new *Pelargonium* plant are stable and reproduced true to type in successive generations.

SUMMARY OF THE INVENTION

Plants of the new *Pelargonium* have not been observed under all possible environmental conditions and cultural conditions. The phenotype may vary somewhat with variations in environmental conditions such as temperature and light intensity without, however, any variance in genotype.

The following traits have been repeatedly observed and are determined to be the unique characteristics of 'Kuegrapidue'. These characteristics in combination distinguish 'Kuegrapidue' as a new and distinct *Pelargonium* plant:

1. Compact and mounding plant habit.
2. Freely branching habit; pinching is not required.
3. Freely flowering habit.
4. Light purple and red purple bi-colored flowers.
5. No cooling treatment required for flower initiation and development.
6. Good container and garden performance.

Plants of the new *Pelargonium* differ primarily from plants of the parent selections in flower color. In addition, plants of the new *Pelargonium* are more freely branching than plants of the parent selections.

Plants of the new *Pelargonium* can be compared to plants of the *Pelargonium crispum* 'Pacbicolor', disclosed in U.S. Plant Pat. No. 14,882. In side-by-side comparisons conducted in Dresden, Germany, plants of the new *Pelargonium* differed from plants of 'Pacbicolor' in the following characteristics:

1. Plants of the new *Pelargonium* were more compact than plants of 'Pacbicolor'.
2. Plants of the new *Pelargonium* had smaller leaves than plants of 'Pacbicolor'.
3. Plants of the new *Pelargonium* and 'Pacbicolor' differed in flower color as plants of 'Pacbicolor' had red purple-colored flowers.

BRIEF DESCRIPTION OF THE PHOTOGRAPH

The accompanying colored photograph illustrates the overall appearance of the new *Pelargonium* plant showing the colors as true as it is reasonably possible to obtain in colored reproductions of this type. Colors in the photograph may differ slightly from the color values cited in the detailed botanical description which accurately describe the colors of the new *Pelargonium* plant. The photograph comprises a side perspective view of a typical flowering plant of 'Kuegrapidue' grown in a container.

DETAILED BOTANICAL DESCRIPTION

The aforementioned photograph and following observations, measurements and values describe plants grown during the summer in 12-cm containers in a glass-covered greenhouse in Dresden, Germany and under cultural practices which closely approximate commercial *Pelargonium* production. During the production of the plants, day and night temperatures averaged 18° C. and light levels averaged 4,500 lux. Plants were 13 weeks old when the photograph and the description were taken. In the detailed description, color references are made to The Royal Horticultural Society Colour Chart, 1995 Edition, except where general terms of ordinary dictionary significance are used.

Botanical classification: *Pelargonium crispum* 'Kuegrapidue'.

Parentage:

*Female, or seed, parent*.—Unnamed proprietary selection of *Pelargonium crispum*, not patented.

*Male or pollen parent*.—Unnamed proprietary selection of *Pelargonium crispum*, not patented.

Propagation:

*Type*.—By vegetative cuttings.

*Time to initiate roots, summer*.—About 18 days at temperatures of 22° C.

*Time to initiate roots, winter*.—About 25 days at temperatures of 22° C.

*Time to produce a rooted young plant, summer*.—About 28 days at temperatures of 18° C.

*Time to produce a rooted young plant, summer*.—About 30 days at temperatures of 20° C.

*Root description*.—Fine, fibrous; creamy white in color.

*Rooting habit*.—Moderate branching; medium density.

Plant description:

*Plant and growth habit*.—Compact and mounded plant habit; broad inverted triangle; relatively short internodes, bushy dense appearance; moderately vigorous growth habit; freely basal branching habit with about five to seven lateral branches developing per plant; pinching is not required.

*Plant height, to top of umbels*.—About 13 cm.

*Plant height, to top of leaves*.—About 11 cm.

*Plant width*.—About 13 cm.

*Lateral branches*.—Length: About 5 cm. Diameter: About 3 mm. Internode length: About 1.4 cm. Strength: Strong. Texture: Pubescent. Color: Close to 146B.

Foliage description:

*Arrangement*.—Alternate; simple.

*Length*.—About 2 cm.

*Width*.—About 2.2 cm.

*Shape*.—Deltoid.

*Apex*.—Emarginate.

*Base*.—Obtuse.

*Margin*.—Serrate.

*Venation pattern*.—Palmate.

*Texture, upper and lower surfaces*.—Pubescent.

*Color*.—Developing leaves, upper surface: Close to 137B. Developing leaves, lower surface: Close to 138A. Fully expanded leaves, upper surface: Close to 137A; venation, close to 137A. Fully expanded leaves, lower surface: Close to 137B; venation, close to 137B.

*Petiole*.—Length: About 1.2 cm. Diameter: About 1 mm. Texture, upper and lower surfaces: Pubescent. Color, upper and lower surfaces: Close to 138B.

Flower description:

*Flower arrangement*.—Single rotate flowers arranged in rounded umbels arising from apical leaf axils; umbels displayed above the foliage on moderately strong peduncles; flowers face mostly upright to outwardly.

*Fragrance*.—Slightly fragrant, aromatic.

*Quantity of flowers*.—Freely flowering habit; about four to six flowers develop per umbel and about eight to ten umbels developing per plant.

*Flowering season*.—In Germany, plants begin flowering in the spring and flowering is continuous throughout the summer and into the autumn; plants do not require a cooling treatment for flower initiation and development; early flowering habit, plants begin flowering about 60 days after planting.

*Flower longevity*.—Individual flowers last about five days on the plant; flowers not persistent.

*Umbel height*.—About 2.5 cm to 3 cm.

*Umbel diameter*.—About 4 cm.

*Flower diameter*.—About 3.2 cm by 2.5 cm.

*Flower depth* (*height*).—About 1 cm.

*Flower buds*.—Length: About 1 cm. Diameter: About 4 mm. Shape: Ovoid. Color: Close to 144A.

*Petals*.—Quantity per flower: Five arranged in a single whorl; two larger upper petals and three smaller lower petals. Length: Upper petals: About 2 cm. Lower petals: About 1.9 cm. Width: Upper petals: About 2.6 cm. Lower petals: About 9 mm. Shape: Obovate. Apex: Obtuse. Base: Attenuate. Margin: Entire. Texture, upper and lower surfaces: Smooth, glabrous. Color, upper petals: When opening and fully opened, upper surface: Close to 59A; venation, close to 59A; color does not fade with development. When opening and fully opened, lower surface: Close to 71C; venation, close to 71C. Color, lower petals: When opening and fully opened, upper surface: Close to 75C; central spot, close to 59A; venation, close to 59A; color does not fade with development. When opening and fully opened, lower surface: Close to 75C; venation, close to 71C.

*Sepals*.—Quantity per flower: Five arranged in a single whorl. Length: About 8 mm. Width: About 4 mm. Shape: Elliptic. Apex: Acuminate. Base: Obtuse. Margin: Entire. Texture, upper and lower surfaces: Smooth. Color, upper and lower surfaces: Close to 146A.

*Peduncle* (*umbel stem*).—Length: About 2.3 cm. Diameter: About 2 mm. Strength: Moderately strong. Angle: Mostly erect. Texture: Smooth. Color: Close to 137B.

*Pedicel* (*individual flower stem*).—Length: About 1.1 cm. Diameter: About 1.5 mm. Strength: Moderately strong. Angle: Mostly erect. Texture: Smooth. Color: Close to 137B.

*Reproductive organs*.—Androecium: Stamen quantity per flower: About five to seven. Filament length: About 1 cm. Filament color: Close to 155B. Anther length: About 2 mm. Anther shape: Ovate. Anther color: Close to 65A. Pollen amount: Moderate. Pollen color: Close to 25B. Gynoecium: Pistil quantity per flower: One. Pistil length: About 1 cm. Stigma shape: Five-parted. Stigma color: Close to 59A. Style length: About 5 mm. Style color: Close to 59B. Ovary color: Close to 142B.

*Seeds and fruits*.—Seed and fruit development have not been observed on plants of the new *Pelargonium*.

Disease & pest resistance: Plants of the new *Pelargonium* have been observed to be resistant to *Puccinia pelargonii-zonalis* and *Xanthomonas campestris* pv. *pelargonii*. Plants of the new *Pelargonium* have not been observed to be resistant to pests and other pathogens common to *Pelargoniums*.

Garden performance: Plants of the new *Pelargonium* have been observed to have good garden performance and to tolerate wind, rain and temperatures ranging from about 5° C. to about 40° C.

It is claimed:

1. A new and distinct *Pelargonium* plant named 'Kuegrapidue' as illustrated and described.

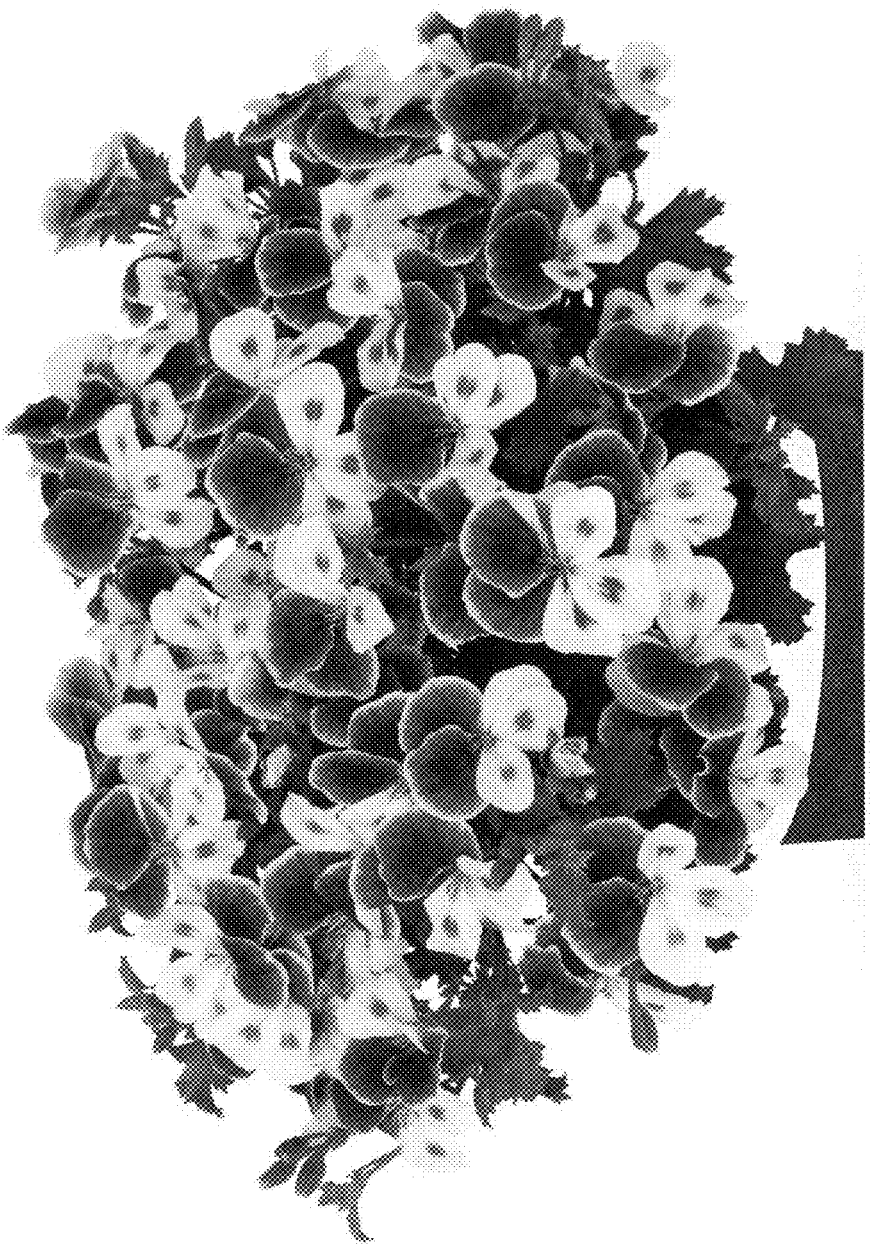

* * * * *